United States Patent
Dane et al.

[11] Patent Number: 6,164,738
[45] Date of Patent: Dec. 26, 2000

[54] STACKING STERILIZING TRAY SYSTEM

[75] Inventors: Gary T. Dane; Valentine T. Faust, III, both of Bow, N.H.; Todd Bettenhausen; Cary Bettenhausen, both of Indianapolis, Ind.

[73] Assignee: Poly Vac, Inc., Manchester, N.H.

[21] Appl. No.: 09/240,112

[22] Filed: Jan. 29, 1999

[51] Int. Cl.[7] .................................................. A47B 88/00
[52] U.S. Cl. .......................... 312/311; 312/213; 312/291; 312/216
[58] Field of Search ..................... 312/311, 310, 312/216, 213, 334.19, 334.21, 334.42, 291, 301, 293.2, 326, 324, 329, 209

[56] References Cited

U.S. PATENT DOCUMENTS

| | | |
|---|---|---|
| 1,195,309 | 8/1916 | White . |
| 1,237,375 | 8/1917 | Parks ................................. 312/291 X |
| 3,203,744 | 8/1965 | Batke et al. . |
| 3,292,986 | 12/1966 | Fenwick ......................... 312/334.19 X |
| 3,399,939 | 9/1968 | Anderson ............................... 312/216 |
| 3,691,634 | 9/1972 | Buchtel et al. . |
| 3,752,547 | 8/1973 | Propst et al. . |
| 3,918,781 | 11/1975 | Paris . |
| 4,118,086 | 10/1978 | Kneier . |
| 4,140,355 | 2/1979 | Swain . |
| 4,389,078 | 6/1983 | Streit . |
| 4,509,805 | 4/1985 | Welsch et al. . |
| 4,681,378 | 7/1987 | Hellman, III . |
| 4,753,495 | 6/1988 | Swink . |
| 4,811,999 | 3/1989 | Remington et al. ................. 312/311 X |
| 4,836,624 | 6/1989 | Schwickrath ............................ 312/216 |
| 4,915,460 | 4/1990 | Nook et al. .......................... 312/216 X |
| 5,048,902 | 9/1991 | Daly . |
| 5,069,466 | 12/1991 | Propst . |
| 5,069,511 | 12/1991 | Swets et al. . |
| 5,211,915 | 5/1993 | Monch . |
| 5,244,272 | 9/1993 | Thompson . |
| 5,350,304 | 9/1994 | Fula et al. . |
| 5,423,605 | 6/1995 | Liu . |
| 5,451,380 | 9/1995 | Zinnanti . |
| 5,472,270 | 12/1995 | Czarnecky et al. . |
| 5,490,975 | 2/1996 | Dane . |
| 5,588,728 | 12/1996 | Eldridge et al. . |
| 5,607,213 | 3/1997 | Slivon et al. ......................... 312/291 X |
| 5,673,984 | 10/1997 | Insalaco et al. . |
| 5,718,491 | 2/1998 | Li . |
| 5,733,026 | 3/1998 | Munachen ....................... 312/334.19 X |
| 5,738,425 | 4/1998 | Rosenberg et al. ................. 312/291 X |
| 5,893,618 | 4/1999 | LePage, Jr. et al. . |

FOREIGN PATENT DOCUMENTS

| | | | |
|---|---|---|---|
| 1322342 | 2/1962 | France .................................. 312/216 |
| 7183 | of 1886 | United Kingdom ................... 312/311 |

Primary Examiner—Janet M. Wilkens
Attorney, Agent, or Firm—Hayes, Soloway, Hennessey, Grossman & Hage, P.C.

[57] ABSTRACT

A storage and sterilization tray assembly for sterilizing, transporting and storing surgical instruments includes a rack having a top, a bottom and four sides, and at least one slidably mounted drawer carried therein. At least one of the sides includes at least one pivotally mounted door which is moveable between a closed position in which the at least one slidably mounted drawer is retained in the rack, and an open position in which the at least one slidably mounted drawer may be slid at least partially out of the rack. The door also serves to stabilize the rack against tipping when in its open position. Preferably, one or more removable trays are carried in the drawer, and the rack includes a plurality of openings in the top, bottom and sides, aligned with openings in the drawer, for permitting ingress and egress of sterilant therethrough.

23 Claims, 10 Drawing Sheets

STACKING STERILIZING TRAY SYSTEM

BACKGROUND OF THE INVENTION

1. Field of the Invention

The present invention relates to sterilizing trays for surgical instruments, and, more particularly, to an improved storage and sterilization tray system for facilitating access to a plurality of trays in a sterilizing, storage or transport case.

2. Background of the Invention

Surgical procedures are regularly performed using "sets" of pre-selected surgical instruments, each set being a collection of instruments established from experience to be useful in a given surgical procedure. The surgical instruments expected to be used in a particular procedure are grouped together to form a set, and, as a set, are sterilized, stored on a pan or tray, and finally transported on that pan or tray to the operating room when their use is required. Complex procedures typically involve a substantial number of instruments. Thus, typically, several instrument trays may be necessary to accommodate all of the required surgical instruments. Accordingly, sterilizing cases often are designed to accommodate a plurality of trays with the instruments arranged on the trays in such a manner that the trays may be accessed as the surgical procedure advances often in a preset sequence.

In the prior art, as shown in FIG. 1, a sterilizing case 110 includes a bottom tray 112, one or more middle trays 114, a top tray 115 and a removable top or lid 110. Latch means 117, 119 is provided for clamping the lid to the base. While stacking tray sterilization cases such as shown in FIG. 1 have become widely adopted, such trays have certain disadvantages. For example, access to a particular tray requires the removal of the tray or trays above it. Requiring prior removal of a tray or trays in order to access the desired tray, could be disruptive to operating room personnel while they hunt for the desired tray. If those instruments sought are buried in a lower positioned tray, precious time again may be lost in the removal, relocation and replacement of the upper trays. In extreme circumstances, precious time lost could compromise the safety of a patient. Also, this could cause wasteful utilization of operating room personnel in the handling of the trays and accessing of certain instruments.

In copending U.S. application Ser. No. 08/897,458, filed Jul. 21, 1997 (now U.S. Pat. No. 5,893,618), there is disclosed a stacking sterilization tray system which overcomes several of the aforesaid disadvantages of prior art systems, such as shown in FIG. 1. More particularly, as shown in FIG. 2, there is provided a stacking sterilization assembly 220 which consists of a rectangularly shaped open rack 222 having a removable end wall or cover 294 for permitting access to the trays 224, 226, 228 which are slidably mounted on rails 230 within the rack so that the trays are accessible from the side of the rack. The rail assemblies preferably are integrally formed with the tray covers 263, 264, 266 and thus serve the dual purpose of covering the tray contents and also supporting the trays. While permitting access to each tray without displacing the others in the rack, the rack requires a end cover and locking mechanism which must first be removed. Also as a tray is pulled out of rack, the weight of the tray and the instruments contained therein could cause the rack to become somewhat unstable.

SUMMARY OF THE INVENTION

Accordingly, it is a primary object of the present invention to overcome the aforesaid problems and disadvantages of the prior art. Another object of the invention is to provide a stacking sterilization tray system having enhanced stability as compared to prior art stacking sterilization tray systems, and which provides quick and unencumbered access to any selected tray or trays in the stack.

The present invention provides a sterilization, transporting and storage container assembly for surgical instruments, and comprising a plurality of drawers for accommodating trays for surgical instruments, and a rack for holding the drawers in a stacked arrangement. Each of the trays is removably positioned on a drawer which in turn is slidably mounted within the rack. The case has hinged doors on either corner of one side, such that when the doors are swung open, each drawer and the tray or trays thereon are slidably accessible from the open side of the rack. In a preferred embodiment of the invention, the open doors stabilize the rack. In the closed position, the doors lock the drawers in position in the rack, i.e. for transportation, sterilization and storage.

Other features, objects and advantages of the present invention will become apparent from the following description of a preferred embodiment of the invention taken in conjunction with the accompanying drawings, wherein like numerals denote like parts, and wherein:

DESCRIPTION OF A PREFERRED EMBODIMENT

Figure 1:
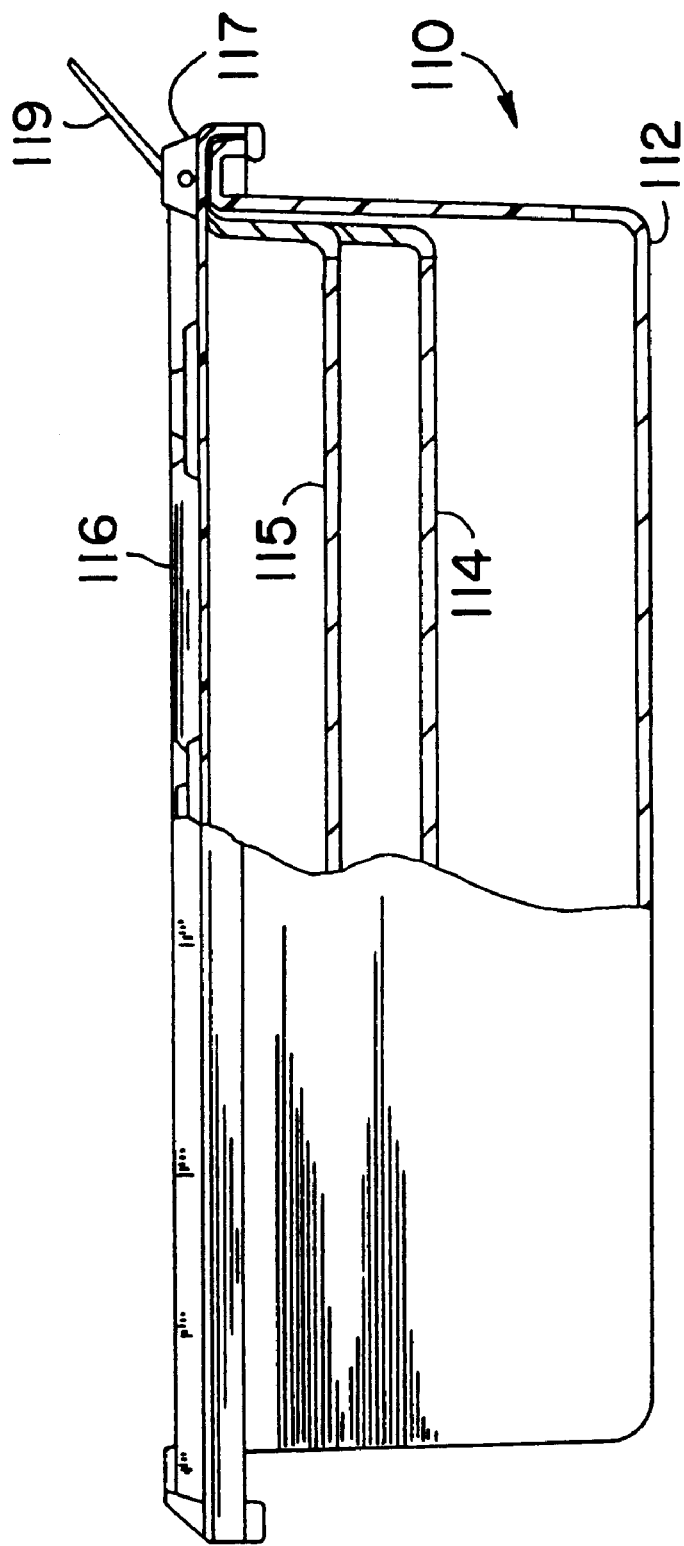
FIG. 1 is a side elevation view, in partial cross-section, of a stacking, multi-tray sterilization, transporting and storage container tray and rack system in accordance with the prior art.
Figure 2:
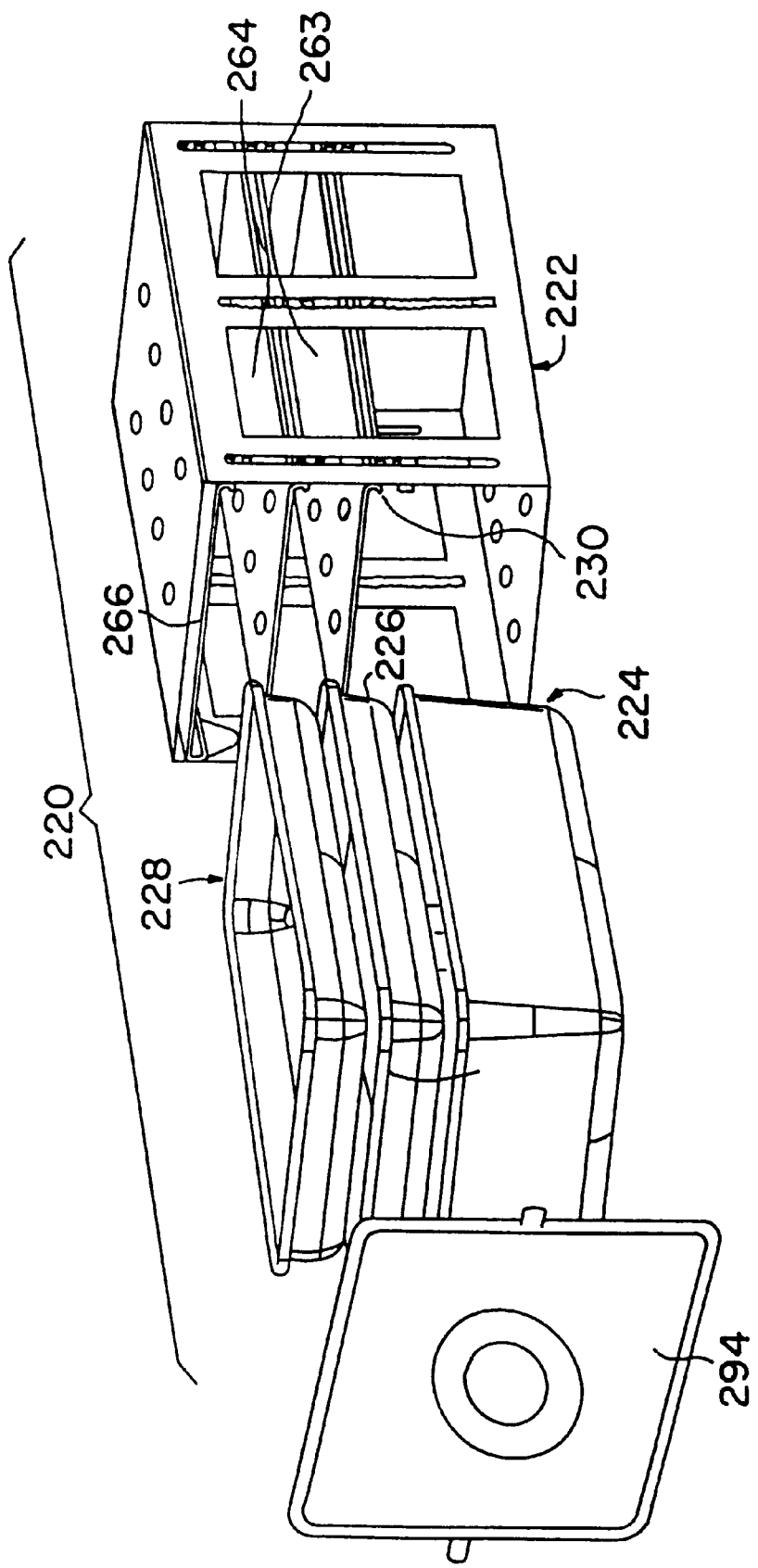
FIG. 2 is perspective view of a stacking, multi-tray sterilization, transporting and storage container tray and rack system in accordance with the prior art.
Figure 3:
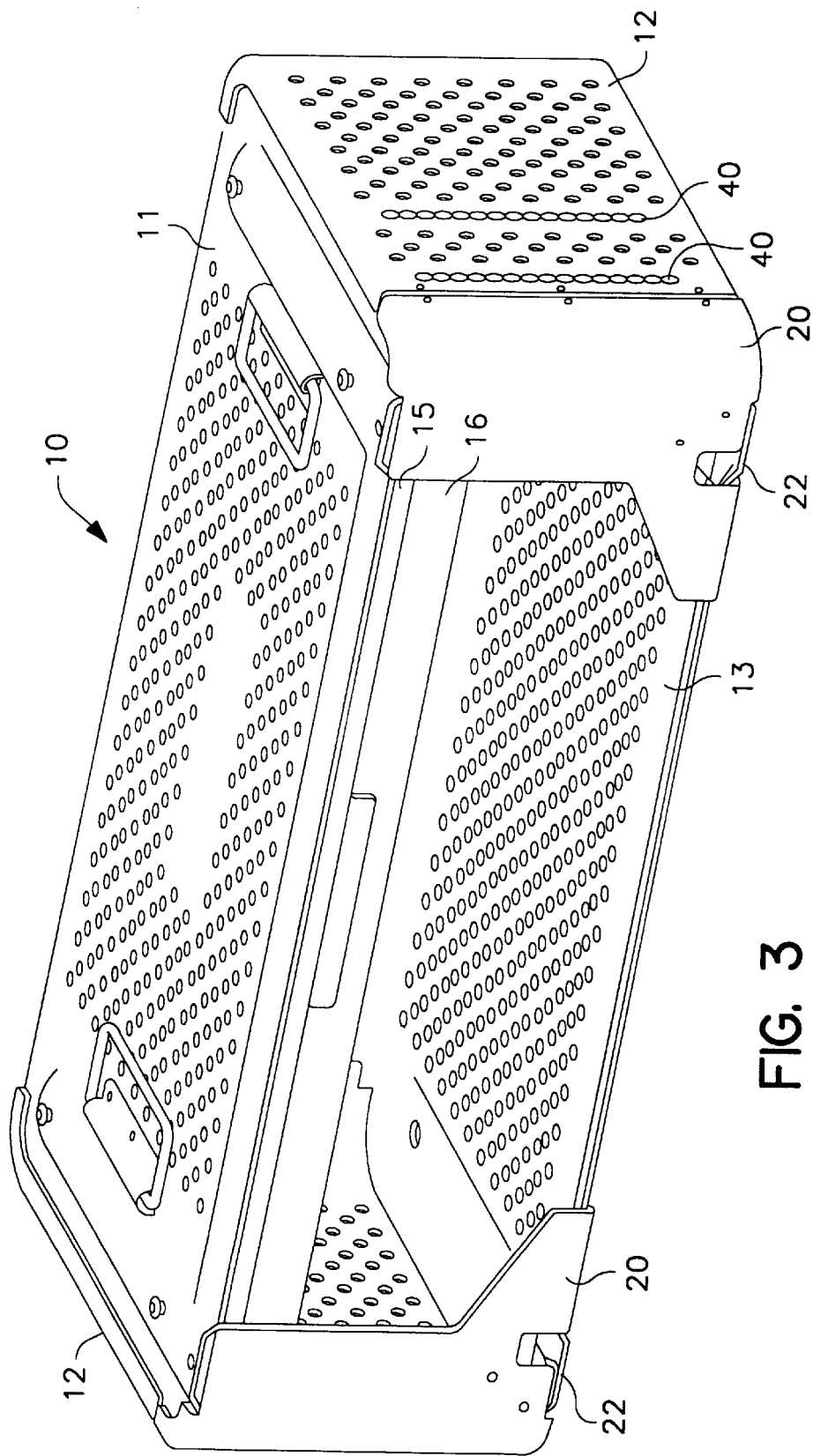
FIG. 3 is a perspective view of a stacking, multi-tray sterilization, transporting and storage assembly system, with the doors closed showing a drawer, tray and rack system made in accordance with the present invention.
Figure 4:
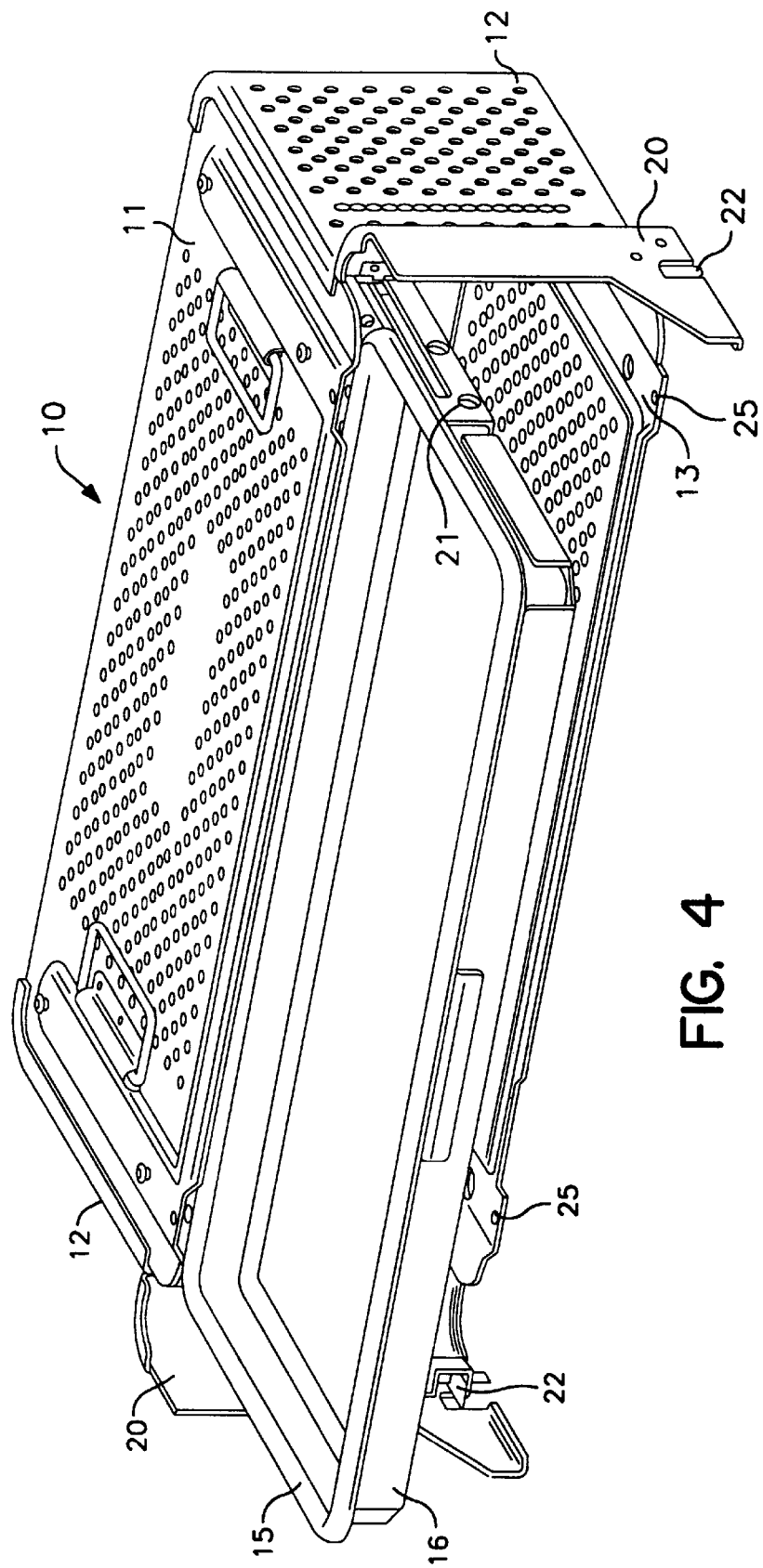
FIG. 4 is a perspective view of the assembly system of FIG. 3 with the doors swung open, and showing details of the tray, drawer a rack in accordance with a preferred embodiment of the invention.
Figure 5:
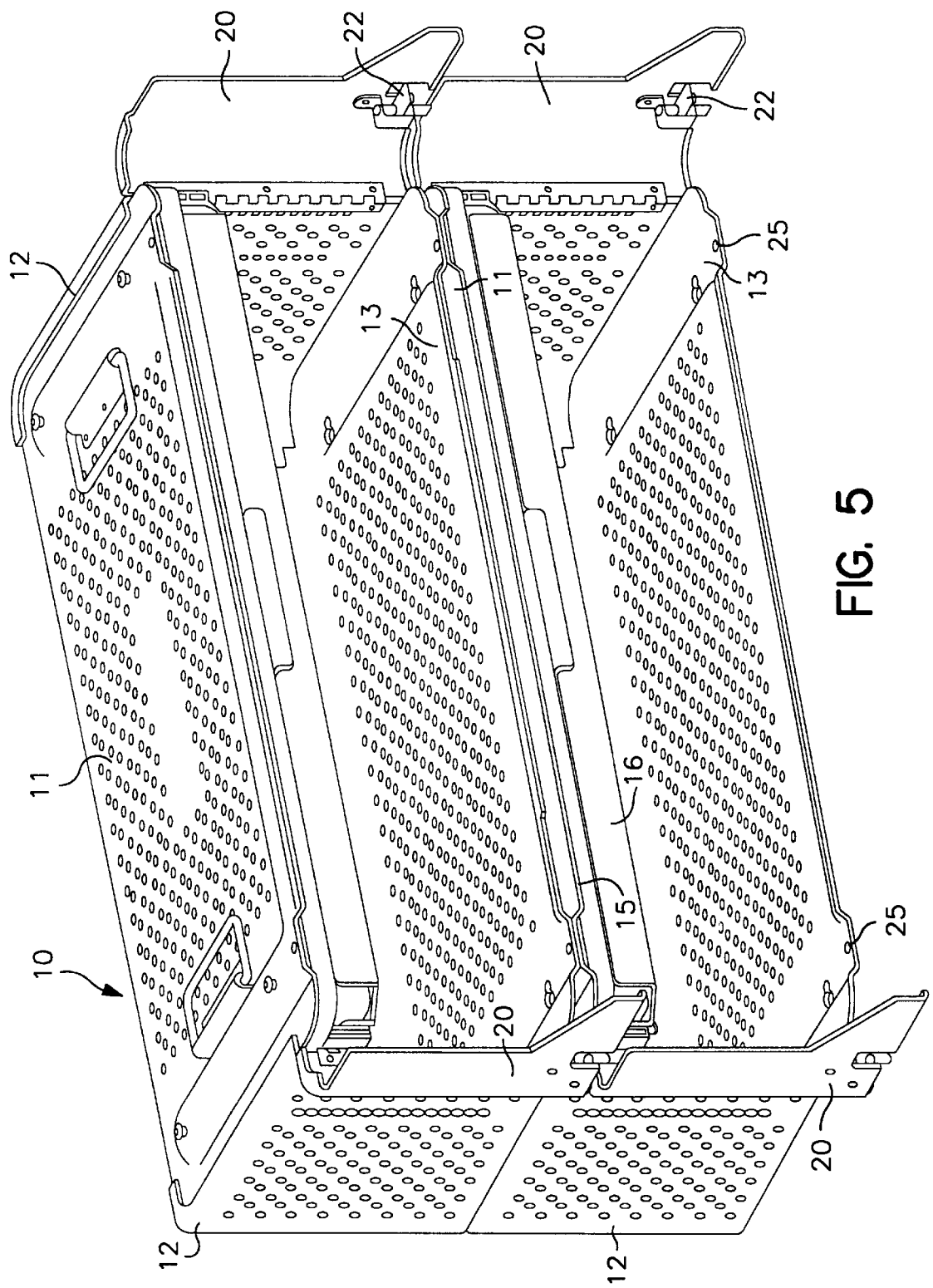
FIG. 5 is a perspective view of two racks shown in FIG. 4 stacked one on top of the other.

Referring to FIGS. 3–5, the sterilization, transporting and storage tray assembly of the present invention consists of a rectangularly shaped rack 10 with an open side and two doors 20 hinged to sides 12 at either end of the open side, and having a removable tray 15 positioned on drawer 16 which is slidably mounted on rails 21 which in turn are mounted on the rack. Top and bottom sides 11 and 13, respectively, of rack 10, preferably comprise a plurality of spaced apertures preferably aligned with the apertures in trays 15 and drawers 16, for permitting ingress and egress of steam of other gaseous sterilants, and allow for condensation drainage.

Figure 6:
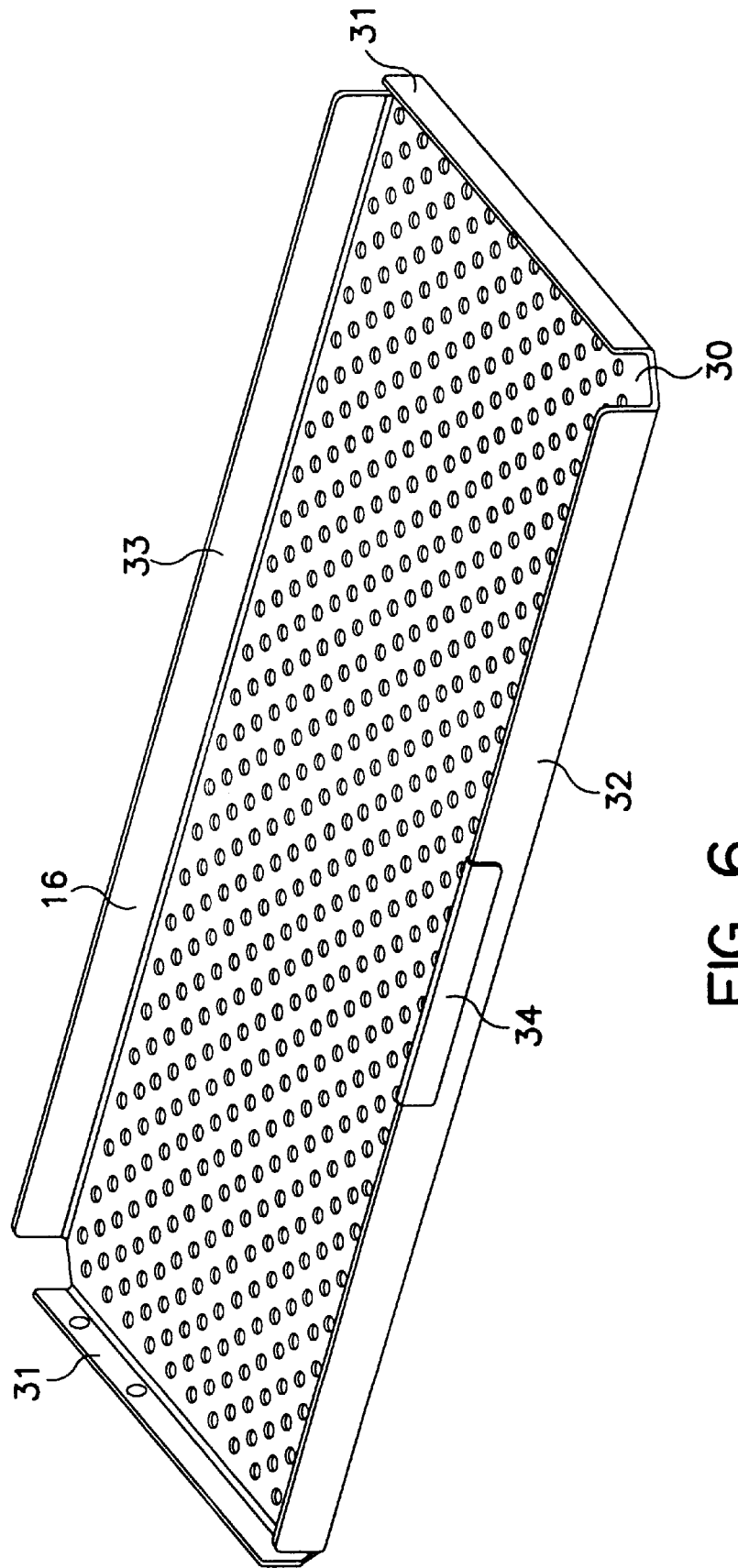
FIG. 6 is a perspective view of a drawer unit of the present invention.

As shown in FIG. 6, drawer 16 consists of a box-like unit having an apertured bottom 30, two generally perpendicular upwardly projecting sidewalls 31, and upwardly projecting opposed front and back walls 32, 33, respectively. Front wall 32 may have a rolled top edge portion 34 to be used as a handle if so desired. The drawer bottom 30 includes a plurality of spaced apertures, typically arranged in a predetermined pattern, for permitting ingress and egress of steam or other gaseous sterilants, and allow for condensation drainage. Preferably, the drawer apertures are aligned with apertures in trays 15 when the latter are carried in the drawers. The drawer bottoms may be dimensioned and shaped to accommodate specific sterilizing tray or trays in accordance with prior art designs although any tray or trays that fit within the drawer may be used.

Figure 6A:
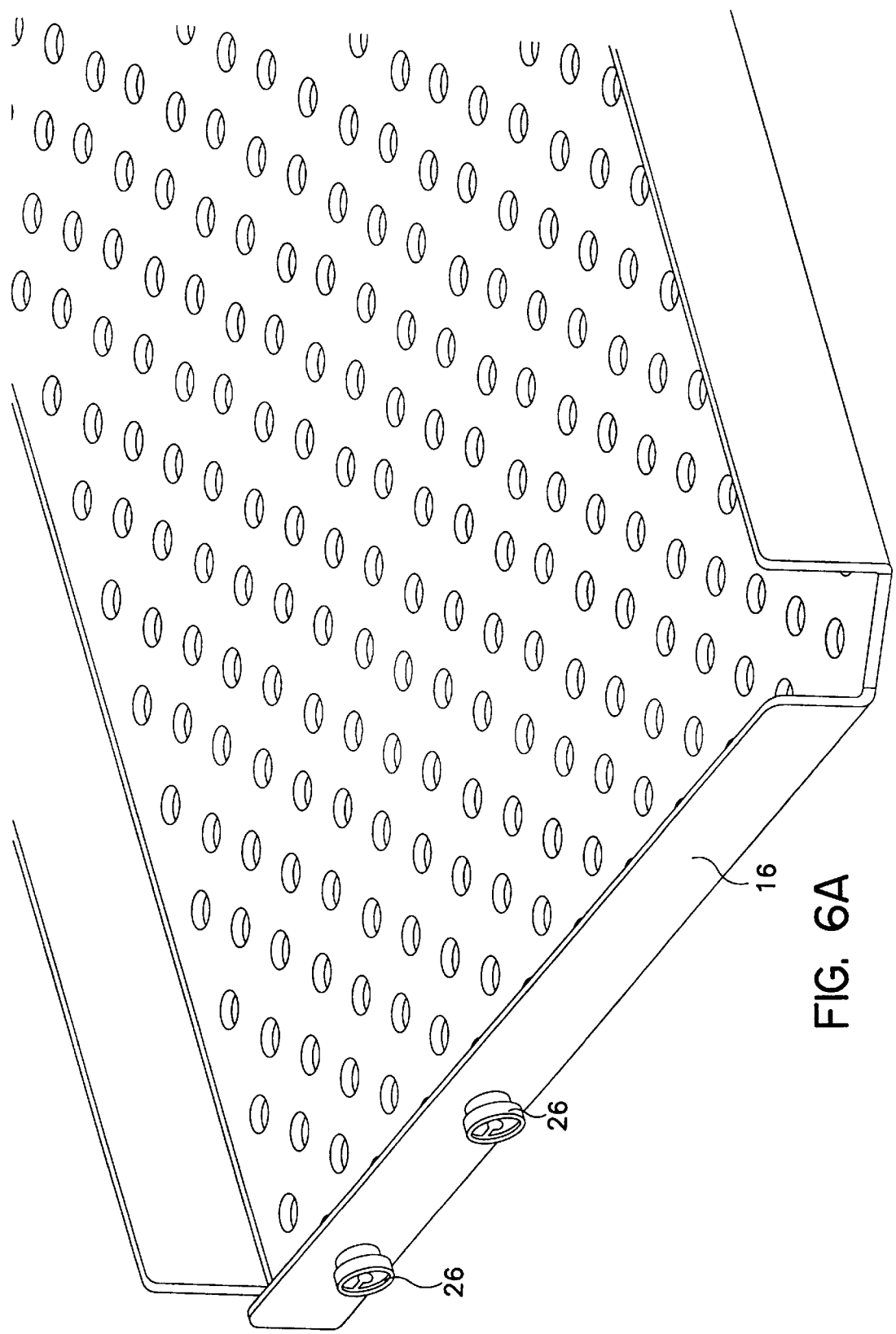
FIG. 6a is an enlarged portion of a drawer showing rollers affixed thereto.

A feature of the present invention and advantage over prior art sterilization, transporting and storage container tray systems is the ability to selectively access any one of the trays in the stack without displacing the other trays. In order to permit such access, as will be shown below, selectively operable closing means 22 are provided for selectively engaging receiving holes 25 in bottom side 13, whereby to allow doors 20 to be swung open to a position substantially perpendicular to the front of the case 10. In the open position, the doors 20 act as supports for and stabilize the rack 10 against tipping. Tray 15 positioned on drawer 16 may be slid out of the rack on rail assemblies 21, whereby to permit access to instruments carried on the trays 15, or to permit removal of the trays 15. Referring to FIG. 6a, in a preferred embodiment of the invention, rollers 26 are affixed to sides 31 of drawer 16 and fit on rail assemblies 21 so as to permit drawer 16 and tray 15 to be slidably pulled from rack 10. Naturally, drawer 16 and tray 15 can easily be pushed back into the rack 10 to permit access to another tray and/or for later storage or transport. Because tray 15 sits atop drawer 16, tray 15 may be removed from the assembly case 10 very easily and without the need to manipulate any fastening mechanisms or the like. When being stored or transported, top 11 doubles as a cover for tray 1 5, the apertures of top 11 being preferably aligned with the apertures in tray 15, and thus also preferably aligned with the apertures in the bottom 13.

Figure 8:
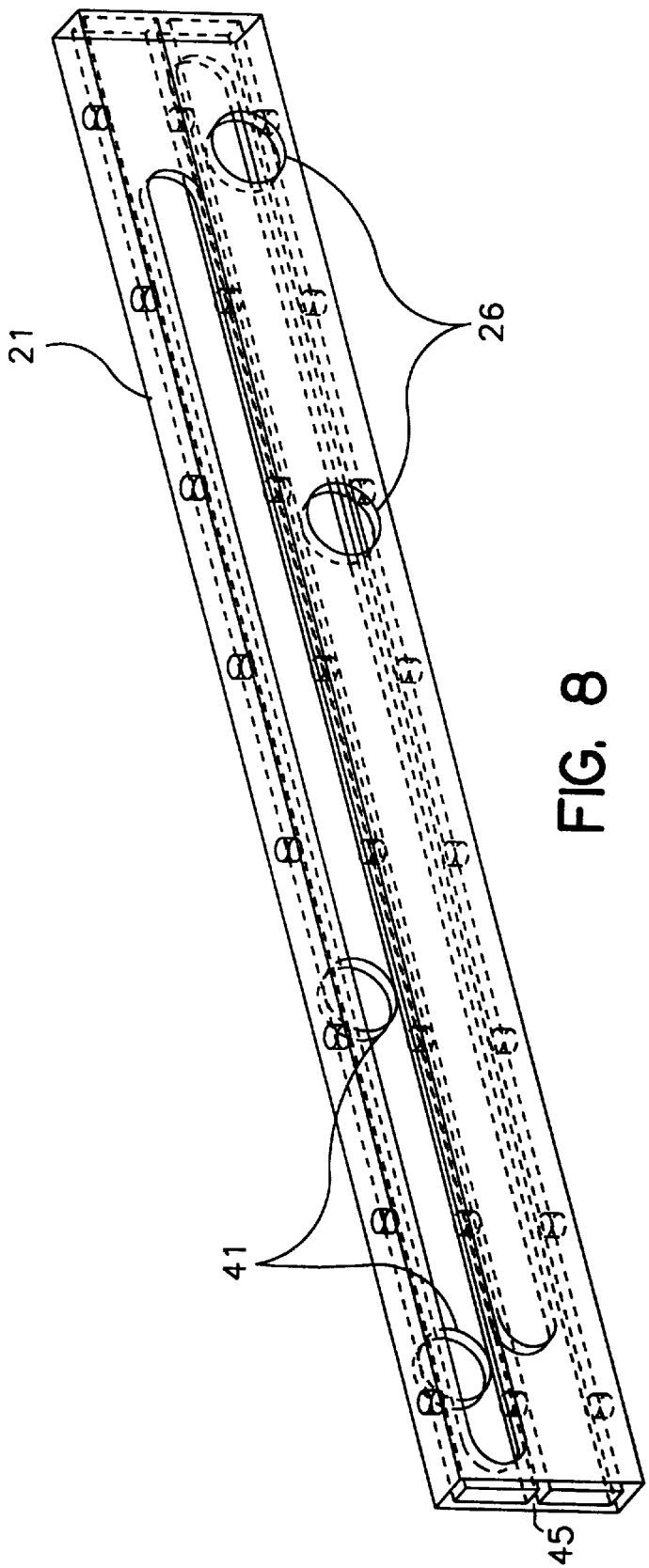
FIG. 8 is a perspective view of a preferred rail assembly made in accordance with the present invention.

Rail assemblies 21 preferably are vertically adjustably mounted in the side walls 12 of rack 10 so as to accommodate different tray height arrangements. Referring in particular to FIG. 8, rail assembly 21 is provided with rollers 41 which are mounted to rack 10 with mounting screws or similar fastening devices (not shown) inserted into rollers 41 through mounting holes 40. Alternatively, rollers 41 of rail assembly 21 may include a shaft with an enlarged tip which extends outward from the center of roller 41which may then be snapped through mounting holes 40 retaining the rollers in place within the rack 10. In this way the rail assemblies are mounted in rack 10 in such manner as to permit the drawer 16 to slide on the rails. In order to remove or reposition a rail assembly, the rollers 41 are separated from the case by removing the mounting screws or otherwise disconnecting the rollers from mounting holes 40, and the rail assembly is then removed from the assembly entirely or repositioned by re-aligning the rollers 41 with other mounting holes 40 and then affixing the rails 21 to the rack 10 by re-inserting the mounting screws or by snapping the rollers 41 into the new position.

Figure 7:
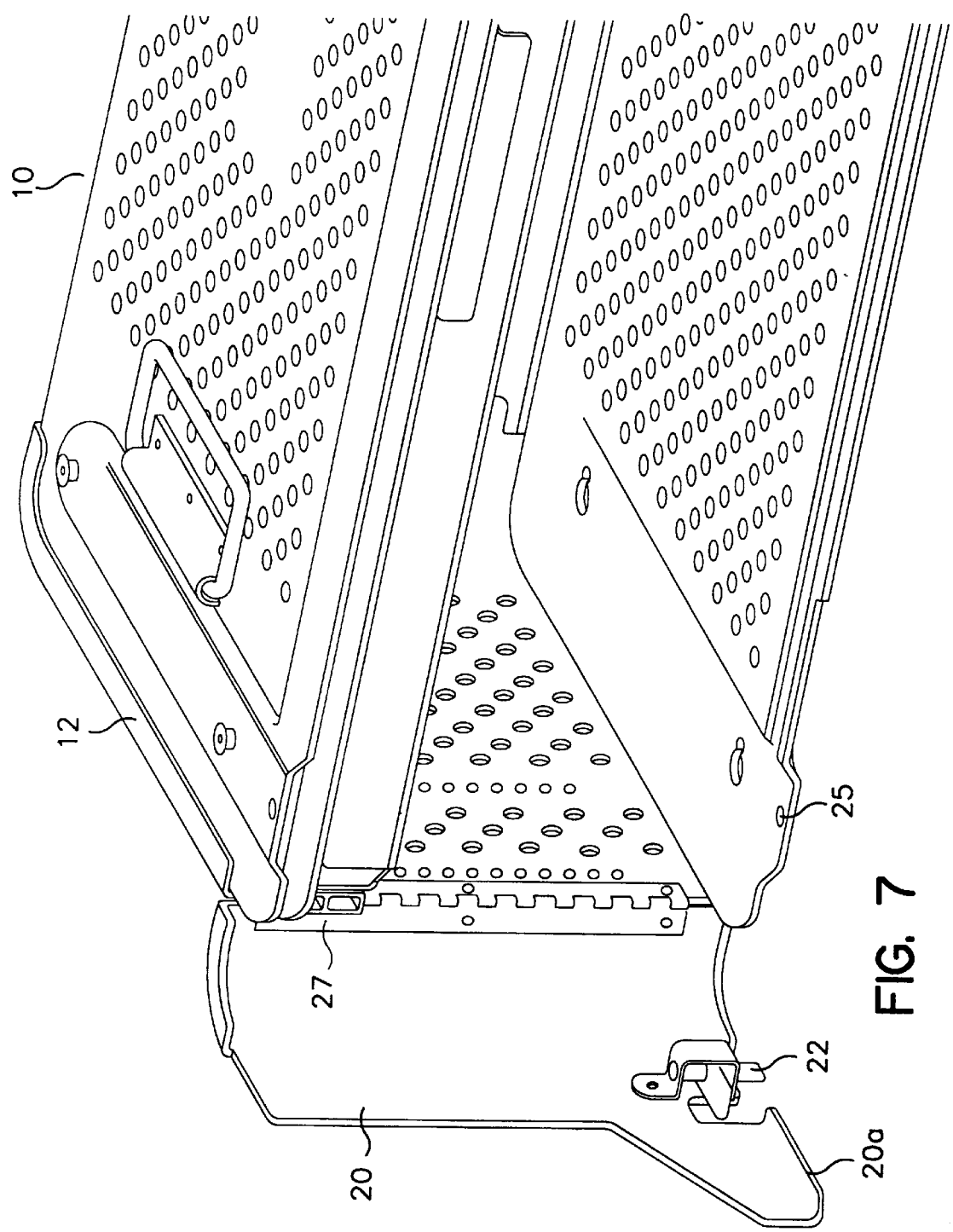
FIG. 7 is also an enlarged portion of a rack made in accordance with a preferred embodiment of the present invention, showing an open door with hinge and closing mechanisms.

FIG. 7 shows details of a single door 20 in the open position, closing means 22 and receiving hole 25. In this embodiment, door 20 is attached to side 12 of rack 10 by hinge 27. It will be appreciated that hinge 27 may be of any number of designs known in the art. Preferably, the hinge end of door 20 is curved so as to provide a rounded edge to rack 10, and the door 20 preferably includes a wing-like extension 20a at its bottom end. Thus, when door 20 is in the open position, the bottom portion of the door 20 and extension 20a provide support for the rack 10 while in use, thus, stabilizing the rack against tipping, e.g. when a heavily loaded tray is pulled out.

Figure 9:
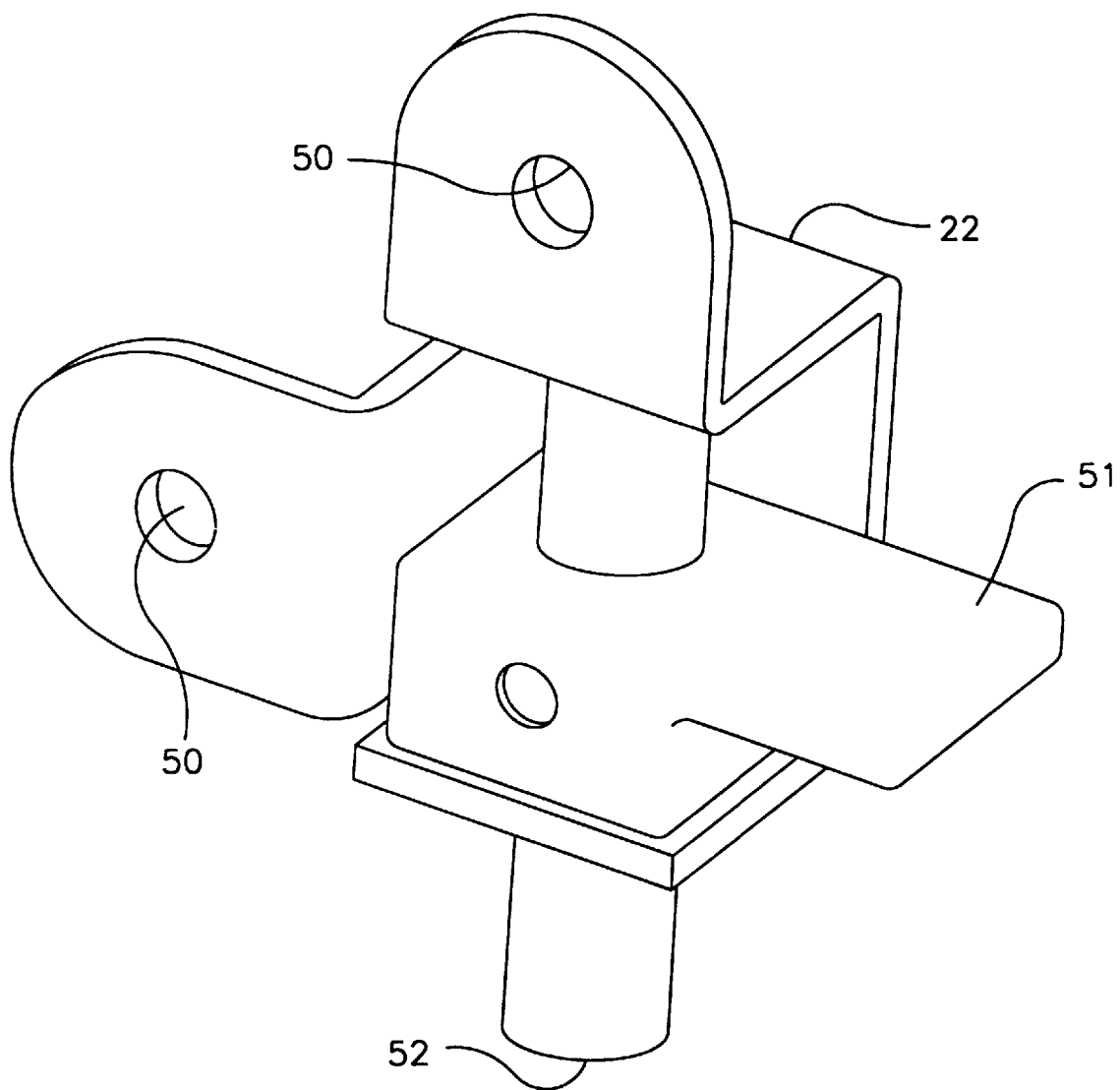
FIG. 9 is an enlarged detail view of a preferred embodiment of a closing means in accordance with the present invention.

FIG. 9 shows details of a preferred embodiment of closing means 22. In this embodiment, closing means 22 is affixed to door 20 with a mounting screw or rivet (not shown) through holes 50. In operation, tab 51 is raised manually such that shaft 52 which extends downward from tab 51 slides upward through an opening in closing means 22 and thereby clears receiving hole 25 in bottom 13 (see FIG. 7) allowing door 20 to be opened. In an alternative embodiment, door 20 may have a lip at the bottom which includes a downward facing boss-like component which formably fits into receiving hole 25 when door 20 is closed. In order to open the door, slight outward pressure will be exerted causing the boss-like component to become displaced from receiving hole 25. The door may be closed by reversing the procedure until the boss-like component engages receiving hole 25. In this closed position, the trays are in a stored position and the case is ready for transport.

Figure 8A:
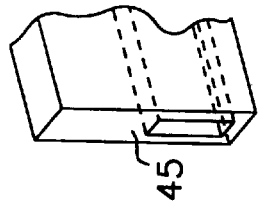
FIG. 8a is a detail view of an alternative embodiment of rail assembly.

The invention is susceptible to modification. For example, as shown in FIG. 8, the trays (not shown) may be provided with rollers 26 affixed directly to the tray sides, and directly fitted onto drawer slide assemblies 21, thereby eliminating the need for separate drawers 16. In this embodiment, as shown in FIG. 8a, rail assembly 21 may be slotted in such fashion so as to allow rollers 26 to be inserted at end 45 of the rail assembly, the opening at one end 45 also having a lip or like construction of appropriate size and tolerance to ensure that tray 15 cannot be displaced from the rack unintentionally. Still other changes are possible. For example, two or more racks may be assembled together, one on top of the other, as shown in FIG. 5. Also, the rack may include only a single door, or doors may be provided on opposite sides. Still other changes may be made without departing from the spirit and scope of the invention.

We claim:

1. A sterilization assembly for sterilizing, transporting and storing surgical instruments, and comprising a rack having a top, a bottom and four sides, and at least one slidably mounted drawer therein, at least one of said sides including at least one pivotally mounted door which is moveable between a closed position in which the at least one slidably mounted drawer is retained in said rack, and an open position in which said at least one slidably mounted drawer may be slid at least partially out of said rack, said at least one door also serving to stabilize the rack against tipping, when the door is in its open position, wherein said at least one door is curved adjacent its pivotally mounted end so as to provide a rounded edge to the rack.

2. A sterilization assembly according to claim 1, and further comprising at least one removable tray carried in said drawer.

3. A sterilization assembly according to claim 1, and comprising two pivotally mounted doors.

4. A sterilization assembly according to claim 1, and including at least one rail adjustably mounted in said rack, for supporting said at least one drawer.

5. A sterilization assembly according to claim 4, wherein said at least one rail is slotted to accommodate rollers.

6. A sterilization assembly according to claim 1, further comprising at least one rail for supporting said at least one drawer, wherein said at least one rail is slotted to accommodate rollers.

7. A sterilization assembly according to claim 1, and comprising a plurality of rails adjustably mounted in said rack, for supporting a plurality of said drawers.

8. A sterilization assembly according to claim 1, and further comprising a closure for locking said at least one door in said closed position.

9. A sterilization assembly according to claim 8, wherein said closure comprises a selectively operable closure means carried on the door for selective fitting into a hole in the rack.

10. A sterilization assembly according to claim 1, wherein said at least one drawer includes a handle.

11. A sterilization assembly according to claim 1, and including a plurality of openings in the top, bottom and sides of said rack for permitting ingress and egress of sterilant therethrough.

12. A sterilization assembly according to claim 11, wherein at least some of said plurality of openings are aligned with one another, and with openings in said drawer and any tray carried therein.

13. A sterilization assembly for sterilizing, transporting and storing surgical instruments, and comprising a rack having a top, a bottom and four sides, and at least one slidably mounted drawer therein, at least one of said sides including at least one pivotally mounted door which is moveable between a closed position in which the at least one slidably mounted drawer is retained in said rack, and an open position in which said at least one slidably mounted drawer may be slid at least partially out of said rack, said at least one door also serving to stabilize the rack against tipping, when the door is in its open position, and further comprising a selectively operable closure carried on the door and movably mounted thereon for selective fitting into a hole in the rack for selectively locking said at least one door in the closed position.

14. A sterilization assembly according to claim 13, and further comprising at least one removable tray carried in said drawer.

15. A sterilization assembly according to claim 13, and comprising two pivotally mounted doors.

16. A sterilization assembly according to claim 13, wherein said at least one door is curved adjacent its pivotally mounted end so as to provide a rounded edge to the rack.

17. A sterilization assembly according to claim 13, and including at least one rail adjustably mounted in said rack, for supporting said at least one drawer.

18. A sterilization assembly according to claim 17, wherein said at least one rail is slotted to accommodate rollers.

19. A sterilization assembly according to claim 13, further comprising at least one rail for supporting said at least one drawer, wherein said at least one rail is slotted to accommodate rollers.

20. A sterilization assembly according to claim 13, and comprising a plurality of rails adjustably mounted in said rack, for supporting a plurality of said drawers.

21. A sterilization assembly according to claim 13, wherein said at least one drawer includes a handle.

22. A sterilization assembly according to claim 13, and including a plurality of openings in the top, bottom and sides of said rack for permitting ingress and egress of sterilant therethrough.

23. A sterilization assembly according to claim 22, wherein at least some of said plurality of openings are aligned with one another, and with openings in said drawer and any tray carried therein.

* * * * *